United States Patent
Park et al.

(10) Patent No.: US 9,597,344 B2
(45) Date of Patent: Mar. 21, 2017

(54) SONOSENSITIVE LIPOSOME, PHARMACEUTICAL COMPOSITION INCLUDING THE SAME, AND METHOD OF DELIVERING ACTIVE AGENT TO SUBJECT USING THE SONOSENSITIVE LIPOSOME

(71) Applicant: Samsung Electronics Co., Ltd., Suwon-si, Gyeonggi-do (KR)

(72) Inventors: Sun Min Park, Seoul (KR); Jungyong Nam, Icheon (KR); Kitae Park, Yongin-si (KR); Hyun Ryoung Kim, Guri-si (KR); Eun Sung Park, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/830,503

(22) Filed: Aug. 19, 2015

(65) Prior Publication Data
US 2015/0352039 A1    Dec. 10, 2015

Related U.S. Application Data

(62) Division of application No. 14/324,818, filed on Jul. 7, 2014, now Pat. No. 9,220,718.

(30) Foreign Application Priority Data

Nov. 29, 2013 (KR) ........................ 10-2013-0147520

(51) Int. Cl.
A61K 9/127    (2006.01)
A61K 31/704    (2006.01)
(Continued)

(52) U.S. Cl.
CPC .......... *A61K 31/704* (2013.01); *A61K 9/0009* (2013.01); *A61K 9/127* (2013.01); *A61K 41/0033* (2013.01); *A61K 47/26* (2013.01)

(58) Field of Classification Search
None
See application file for complete search history.

(56) References Cited

U.S. PATENT DOCUMENTS 5,736,531 A * 4/1998 von Borstel ......... A61K 31/513
514/49
6,054,441 A * 4/2000 von Borstel ........... A61K 31/70
424/78.17

(Continued)

FOREIGN PATENT DOCUMENTS

EP    0243947 A1    11/1987
WO    99/39738 A1    8/1999

OTHER PUBLICATIONS

DD Lasic, PM Frederik, MCA Stuart, Y Barenholz, TJ McIntosh. "Gelation of Liposome Interior: A Novel Method for Drug Encapsulation." Federation of European Biochemical Societies Letters, vol. 312, No. 2,3, Nov. 1992, pp. 255-258.*

(Continued)

*Primary Examiner* — Isaac Shomer
(74) *Attorney, Agent, or Firm* — Leydig, Voit & Mayer, Ltd.

(57) ABSTRACT

Provided is a liposome comprising a lipid bilayer and a sonosensitizer that is disposed in and/or on the lipid bilayer, wherein the sonosensitizer self-assembles to form aggregates when exposed to ultrasound; and a method of efficiently delivering an active agent to a target site in the body of a subject using the sonosensitive liposome.

8 Claims, 2 Drawing Sheets

(51) Int. Cl.
    A61K 41/00    (2006.01)
    A61K 9/00     (2006.01)
    A61K 47/26    (2006.01)

(56) References Cited

U.S. PATENT DOCUMENTS

| | | |
|---|---|---|
| 6,200,598 B1 | 3/2001 | Needham |
| 7,672,704 B2 | 3/2010 | Viglianti et al. |
| 7,769,423 B2 | 8/2010 | Viglianti et al. |
| 7,901,709 B2 | 3/2011 | Needham |
| 8,435,558 B1 | 5/2013 | Hood et al. |
| 2004/0247663 A1 | 12/2004 | Zalipsky et al. |
| 2005/0090732 A1* | 4/2005 | Ivkov .................. A61N 1/406 600/411 |
| 2007/0207194 A1 | 9/2007 | Grayburn et al. |
| 2009/0098212 A1 | 4/2009 | Fossheim et al. |
| 2009/0246127 A1 | 10/2009 | Hummel et al. |
| 2011/0177009 A1 | 7/2011 | Langereis et al. |
| 2011/0200665 A1 | 8/2011 | Mei et al. |
| 2012/0045397 A1 | 2/2012 | Liu |
| 2012/0121695 A1 | 5/2012 | Lauten et al. |
| 2012/0189689 A1 | 7/2012 | Lauten et al. |
| 2012/0288557 A1 | 11/2012 | Evjen et al. |

OTHER PUBLICATIONS

G Cravotto, P Cintas. "Molecular self-assembly and patterning Induced by sound waves. The case of gelation." Chemical Society Reviews, vol. 38, 2009, pp. 2684-2697.*

SM Park, BH Kim. "Ultrasound-triggered water gelation with a modofied nucleoside." Soft Matter, vol. 4, 2008, pp. 1995-1997.*

Cravotto et al., Molecular self-assembly and patterning induced by sound waves. The case of gelation, *Chemical Society Reviews*, 38: 2684-2697-1973 (2009).

Lasic et al., "Gelation of Liposome Interior: A Novel Method for Drug Encapsulation", *Federation of European Biochemical Societies Letters*, 312 (2,3):255-258 (1992).

Park et al., "Ultrasound-triggered water gelation with a modified nucleoside", *Soft Matter*, 4: 1995-1997 (2008).

Schroeder et al., Ultrasound, liposomes, and drug delivery: principles for using ultrasound to control the release of drugs from liposomes, *Chemistry and Physics of Lipids*, 162: 1-16 (2009).

Wu et al., "Ultrasound Switch and Thermal Self-Repair of Morphology and Surface Wettability in a Cholesterol-Based Self-Assembly System", *Angewandte Chemie International Edition*, 47: 1063-1067 (2008).

Wu et al., "Ultrasound Switch and Thermal Self-Repair of Morphology and Surface Wettability in a Cholesterol-Based Self-Assembly System", *Angewandte Chemie International Edition*, 47: cover page and S1-S16 (2008).

Wu et al., "Tunable Gel Formation by both Sonication and Thermal Processing in a Cholesterol-Based Self-Assembly System", *Chemistry A European Journal*, 15: 6234-6243 (2009).

Yamashita, T. et al., "A novel bubble liposome and ultrasound-mediated gene transfer to ocular surface: RC-1 cells in vitro and conjunctiva in vivo," *Experimental Eye Research* 85, 741-748 (2007).

* cited by examiner

US 9,597,344 B2

SONOSENSITIVE LIPOSOME, PHARMACEUTICAL COMPOSITION INCLUDING THE SAME, AND METHOD OF DELIVERING ACTIVE AGENT TO SUBJECT USING THE SONOSENSITIVE LIPOSOME

CROSS-REFERENCE TO RELATED APPLICATION

This application claims the benefit of Korean Patent Application No. 10-2013-0147520, filed on Nov. 29, 2013, in the Korean Intellectual Property Office, the entire disclosure of which is hereby incorporated by reference.

BACKGROUND

1. Field

The present disclosure relates to sonosensitive liposomes, pharmaceutical compositions including the same, and methods of efficiently delivering an active agent to a subject using the sonosensitive liposomes.

2. Description of the Related Art

Liposomes have at least one lipid bilayer membrane enclosing an aqueous internal compartment. Liposomes may be characterized by membrane type and by size. Small unilamellar vesicles (SUVs) have a single membrane and have a diameter in a range from about 20 nm and to about 50 nm. Large unilamellar vesicles (LUVs) may have a diameter of at least 50 nm. Oligolamellar large vesicles and multilamellar vesicles have multiple, usually concentric, membrane layers, and may have a diameter of at least 100 nm. Liposomes with several nonconcentric membranes, i.e., several smaller vesicles contained within a larger vesicle, are termed multivesicular vesicles.

Liposomes are formulated to carry drugs or other active agents either contained within an aqueous interior space (water-soluble active agents) or partitioned into the lipid bilayer (water-insoluble active agents). In addition, hydrophobic materials such as cholesterols are contained in a micelle, and the micelle may be contained in the liposome interior space.

Ultrasound-enhanced drug delivery is non-invasive and is carefully concentrated and controlled, and accordingly, such drug delivery may have several advantages including drugs may be penetrated to a target site deep in the body. Here, use of initial ultrasound in helping drug delivery was transcutaneous.

Therefore, in order to efficiently deliver active agents such as drugs, new sonosensitive liposomes have been required.

BRIEF SUMMARY

Provided is a liposome comprising a lipid bilayer; and a sonosensitizer that is disposed in and/or on the lipid bilayer, wherein the sonosensitizer self-assembles to form aggregates when exposed to ultrasound.

Also provided is a method of delivering an active agent to a subject, the method comprising administering the liposome provided herein to a subject, and applying ultrasound to the liposome to release the active agent.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
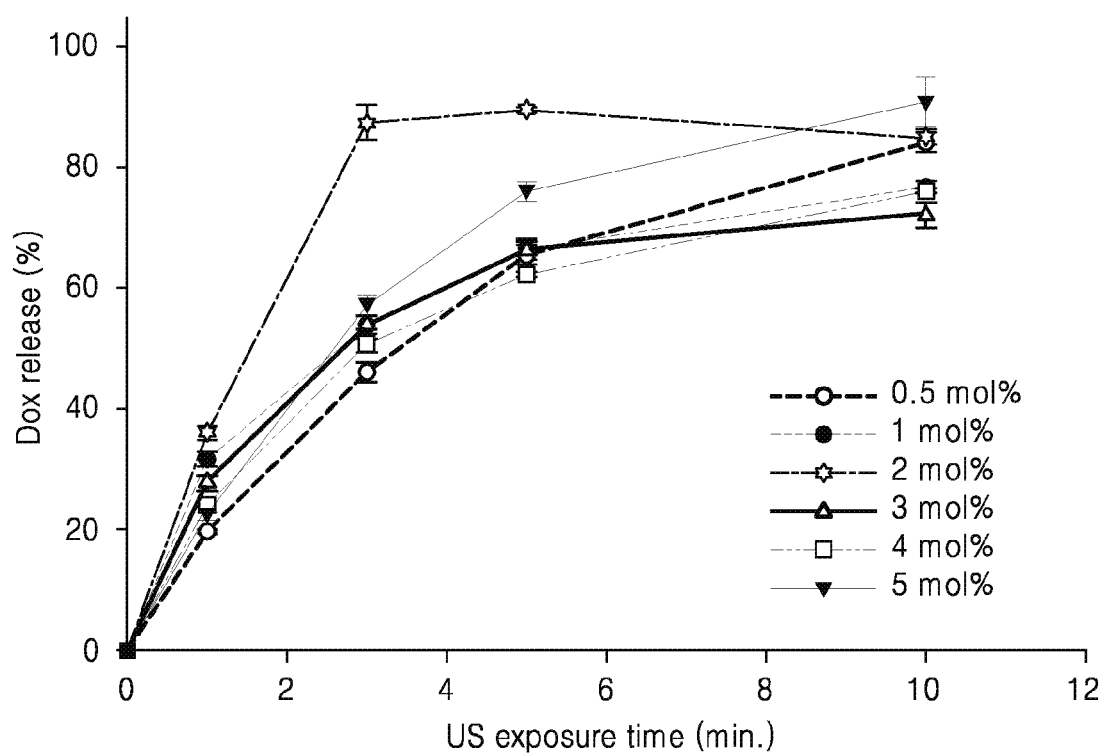
FIG. 1 is a graph showing the extent of drug release, according to the amount of sonosensitizer and ultrasound exposure time used.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, a sonosensitive liposome includes a lipid bilayer and a sonosensitizer disposed in and/or on the lipid bilayer, wherein the sonosensitizer self-assembles to form aggregates, when exposed to ultrasound.

The term "liposome" as used herein indicates an artificially and/or naturally prepared vesicle formed of a lipid bilayer. A liposome may be in a form of unilamellar vesicles or multilamellar vesicles.

The liposome may be a sonosensitive liposome. The sonosensitive liposome refers to a liposome that increases permeability thereof when exposed to ultrasound. In this regard, when the sonosensitive liposome is exposed to ultrasound, an active agent that is contained in the sonosensitive liposome may be released. In some embodiments, the liposome may be non-sensitive to temperatures. The active agent-containing liposome may not have permeability changes of more than 10% at a temperature ranging between about 25° C. and about 45° C., for example, more than 8%, more than 6%, more than 4%, more than 3%, more than 2%, more than 1%, or more than 0.5%.

Ultrasound may be a wave with a frequency greater than an audio frequency of about 16 Hz to about 20 kilohertz (kHz). Ultrasound may be high intensity focused ultrasound (HIFU), high non-intensity focused ultrasound, or a combination thereof. HIFU is ultrasound involving high-intensity ultrasound energies in one place to create a concentrated focus. HIFU may be ultrasound-guided HIFU or magnetic resonance imaging (MRI)-guided HIFU. Ultrasound may have a frequency, for example, in a range from about 20 kHz to about 2.0 megahertz (MHz), about 40 kHz to about 2.0 MHz, about 60 kHz to about 2.0 MHz, about 80 kHz to about 2.0 MHz, about 100 kHz to about 2.0 MHz, about 150 kHz to about 2.0 MHz, about 200 kHz to about 2.0 MHz, about 250 kHz to about 2.0 MHz, about 300 kHz to about 2.0 MHz, about 350 kHz to about 2.0 MHz, about 400 kHz to about 2.0 MHz, about 450 kHz to about 2.0 MHz, about 500 kHz to about 2.0 MHz, about 550 kHz to about 2.0 MHz, about 600 kHz to about 2.0 MHz, about 650 kHz to about 2.0 MHz, about 700 kHz to about 2.0 MHz, about 750 kHz to about 2.0 MHz, about 800 kHz to about 2.0 MHz, about 850 kHz to about 2.0 MHz, about 900 kHz to about 2.0 MHz, about 950 kHz to about 2.0 MHz, about 1.0 MHz to about 2.0 MHz, about 1.1 MHz to about 1.9 MHz, about 1.2 MHz to about 1.8 MHz, about 1.3 MHz to about 1.7 MHz, or about 1.4 MHz to about 1.6 MHz.

The term "lipid bilayer" as used herein refers to a membrane made of two layers of lipid molecules. The lipid bilayer may have a thickness similar with that of a naturally existing membrane, such as a cell membrane, a nuclear membrane, and a virus envelop. For example, the thickness of the lipid bilayer may be 10 nm or less, for example, in a range from about 1 nm to about 9 nm, about 2 nm to about 8 nm, about 2 nm to about 6 nm, about 2 nm to about 4 nm, or about 2.5 nm to about 3.5 nm. The lipid bilayer is a barrier that keeps ions, proteins, and other molecules where they are needed and prevents them from diffusing into areas where they should not be. The "lipid molecule" for constructing the lipid bilayer may be a molecule having a hydrophilic head and hydrophobic tails. The lipid molecule may have 14 to 50 carbon atoms.

The lipid bilayer may be, but is not limited to, a phospholipid, a lipid conjugated to polyethylene glycol (PEG), cholesterol, or any combination thereof.

The phospholipid is a complex lipid containing phosphate ester within a molecule. Also, the phospholipid is a main component of biological membranes, such as a cell membrane, endoplasmic reticulum, mitochondria, and myelin sheath around nerve fibers. The phospholipid has a hydrophilic head and two hydrophobic tails. When the phospholipids are exposed to water, they arrange themselves into a two-layered sheet (bilayer) with all of their tails pointing toward the center of the sheet. The center of this bilayer contains almost no water, and also excludes molecules like sugars or salts that dissolve in water but not in oil. The phospholipid with a certain head group may alter the surface chemistry of the bilayer. In addition, the lipid tails may affect membrane properties, for instance by determining the phase of the bilayer. The lipid bilayer may adopt a solid gel phase sate at lower temperatures, but undergo phase transition to a fluid state at higher temperatures. The packing of lipids within the lipid bilayer may also affect mechanical properties thereof, including resistance to stretching and bending. A biological membrane may include several types of lipids other than the phospholipids.

The phospholipids may include phosphatidic acid, phosphatidylethanolamine, phosphatidylcholine, phosphatidylserine, phosphatidylinositol, phosphosphingolipid, or any combination thereof. Phosphatidylcholine (PC) may include choline as a head group and glycerophosphoric acid as a tail, wherein glycerophosphoric acid may be saturated fatty acid or unsaturated fatty acid, and have 14 to 50 carbon atoms. Examples of the PC include 1,2-dipalmitoyl-sn-glycero-3-phosphocholine (DPPC), 1,2-distearoyl-sn-glycero-3-phosphocholine (DSPC), egg PC, soy bean PC, or any combination thereof. The phospholipid may include, for example, DPPC and egg PC at a ratio ranging from about 4:1 to about 1:4, about 3:1 to about 1:3, or about 2:1 to about 1:2. For example, the phospholipid may include DPPC and egg PC at a ratio of 1:1.

The lipid conjugated to polyethylene glycol (PEG) may be, for example, phosphatidylethanolamine (PE)-PEG. The PE may be saturated fatty acid, unsaturated fatty acid, a mixed acyl chain, lysophosphatidylethanolamine, or any combination thereof. The lipid conjugated to PEG may be, for example, 1,2-distearoylphosphatidylethanolamine-methyl-polyethylene glycol (DSPE-PEG).

The term "cholesterol" as used herein refers to any one of steroid compounds. The cholesterol may also include a cholesterol derivative, and examples thereof include sitosterol, ergosterol, stigmasterol, 4,22-stigmastadiene-3-on, stigmasterol acetate, lanosterol, cycloartenol, or any combination thereof. The cholesterol may enhance stability of a lipid bilayer and assist to lower permeability of the lipid bilayer.

The term "primary lipid" as used herein refers to a main lipid component of a liposome bilayer material in a liposome bilayer. Thus, for example, in a liposome bilayer in which 70% is phospholipid and 30% is cholesterol, the primary lipid is the phospholipid.

The sonosensitizer may be a material that increases the permeability of the liposomes when the liposomes are exposed to ultrasound. The increase in the permeability of the liposomes may be induced by the sonosensitizer, the sonosensitizer being self-assembled to form aggregates when exposed to ultrasound. That is, by the formation of aggregates, there may be formed a pore space in and/or on the lipid bilayer of the liposomes.

The sonosensitizer may have Formula (I) below:

<Formula (I)>

$$A\text{-}B\text{-}C \qquad (I)$$

In Formula (I), A is may be a moiety including an aromatic ring, B may be a moiety including hydrogen bond donor and acceptor, and C may be a hydrophobic moiety including 8 to 40 carbon atoms.

In Formula (I), A may be an unsubstituted or substituted $C_6$-$C_{30}$ aryl group or an unsubstituted or substituted $C_3$-$C_{30}$ heteroaryl group. A may be, for example, a polycyclic aromatic hydrocarbon, and more particularly, a polycyclic aromatic hydrocarbon including at least two or three rings. A may induce π-π stacking interactions between the sonosensitizers, and accordingly, the self-assembly of the sonosensitizers may be induced. The self-assembly may also enhance the permeability of the liposomes. A may be a group having carbon numbers C3 to C30, C3 to C20, C3 to C15, C3 to C10, C4 to C30, C4 to C20, C4 to C15, C4 to C10, C5 to C30, C5 to C20, C5 to C15, C5 to C10, C6 to C30, C6 to C25, C6 to C20, C6 to C15, or C6 to C12.

The term "aryl" as used herein is used alone or in combination, and refers to an aromatic hydrocarbon group having one or more rings.

The term "aryl" also refers to a group in which an aromatic ring is fused to one or more cycloalkyl rings.

Examples of "aryl" include phenyl, naphthyl, and anthracene. At least one hydrogen atom of the aryl group may be substituted with a halogen atom, a $C_1$-$C_{20}$ alkyl group substituted with a halogen atom (e.g., $CCF_3$, $CHCF_2$, $CH_2F$, and $CCl_3$), a $C_1$-$C_{20}$ alkoxy group, a $C_2$-$C_{20}$ alkoxyalkyl group, a hydroxy group, a nitro group, a cyano group, an amino group, an amidino group, a hydrazine group, a hydrazone group, a carboxyl group or a salt thereof, a sulfonyl group, a sulfamoyl, a sulfonic acid group or a salt thereof, a phosphoric acid or a salt thereof, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, a $C_7$-$C_{20}$ heteroarylalkyl group, a $C_6$-$C_{20}$ heteroaryloxy group, a $C_6$-$C_{20}$ heteroaryloxyalkyl group, or a $C_6$-$C_{20}$ heteroarylalkyl group. The substituents may have 1 to 20 carbon atoms, for example, 1 to 15 carbon atoms, 1 to 10 carbon atoms, 1 to 10 carbon atoms, 1 to 5 carbon atoms, 2 to 20 carbon atoms, 2 to 15 carbon atoms, 2 to 10 carbon atoms, 2 to 5 carbon atoms, 3 to 20 carbon atoms, 3 to 15 carbon atoms, 3 to 10 carbon atoms, 3 to 5 carbon atoms, 5 to 20 carbon atoms, 5 to 15 carbon atoms, 5 to 10 carbon atoms, 6 to 20 carbon atoms, 6 to 15 carbon atoms, or 6 to 10 carbon atoms.

The term "heteroaryl" as used herein refers to a monocyclic or bicyclic organic group that contains at least one ring where one or more hetero atoms selected from N, O, P, and S are ring atoms, and the remaining ring atoms are carbon atoms. The heteroaryl group may include, for example, 1 to 5 hetero atoms, and 5 to 10 ring members.

S or N may be oxidized to various oxidation states.

Typical monocyclic heteroaryl groups may include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, 2-pyrazin-2-yl, pyrazin-4-yl, pyrazin-5-yl, 2-pyrimidin-2-yl, 4-pyrimidin-2-yl, or 5-pyrimidin-2-yl.

The term "heteroaryl" also refers to a group in which a heteroaromatic ring is fused to one or more aryl, cyclyaliphatic, or heterocyclic rings.

Examples of bicyclic heteroaryl include purinyl, indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

At least one hydrogen atom of the "heteroaryl" group may be substituted with the same substituents as described above in connection with the aryl group.

In Formula (I), A may be, for example,

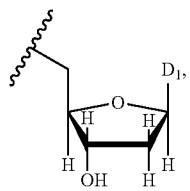 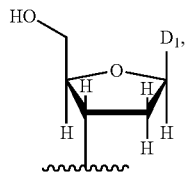

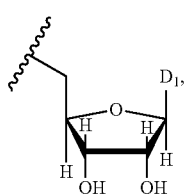 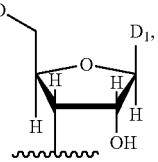 or

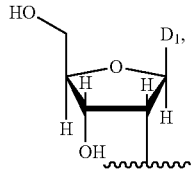

wherein $D_1$ may be

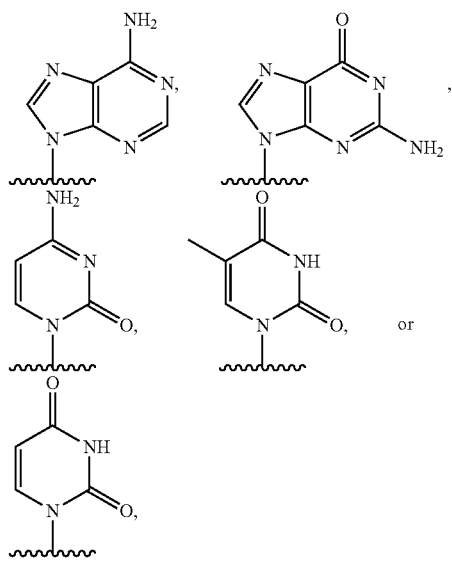

in which at least one hydrogen atom of D1 may be substituted the same substituent as described above in connection with the aryl group. In Formula (I), A may be also

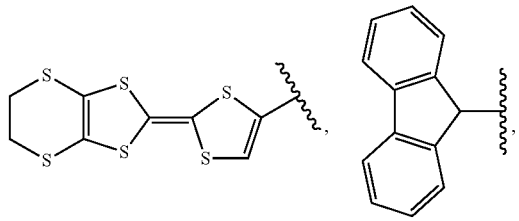

or

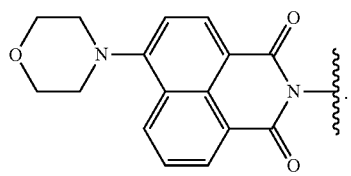

In Formula (I), B may be —NH—C(O)—NH—, —O—C(O)—, —NH—C(O)—, —CH(COOH)—, —NH—C(O)—O—, —S—, or a $C_1$-$C_{20}$ aliphatic hydrocarbon including at least one substituent selected from the group consisting of —NH—C(O)—NH—, —O—C(O)—, —NH—C(O)—, —CH(COOH)—, —NH—C(O)—O—, and —S—. The $C_1$-$C_{20}$ aliphatic hydrocarbon may be a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group. At least one hydrogen atom of the "$C_1$-$C_{20}$ aliphatic hydrocarbon" may be substituted with the same substituents as described above in connection with the aryl group. In Formula (I), B may include, for example, at least one selected from the group consisting of —NH—C(O)—NH—, —(CH$_2$)—O—C(O)CH$_2$CH(COOH)—, —S(CH$_2$)CH$_2$NHC(O)NH—, —(CH$_2$)$_2$NHC(O)(CH$_2$)$_3$NHC(O)O—, and —(CH$_2$)$_6$NHC(O)O—.

In Formula (I), C may be a hydrophobic moiety including 8 to 40 carbon atoms. The hydrophobic moiety including 8 to 40 carbon atoms may be selected from a substituted or unsubstituted $C_1$-$C_{40}$ alkyl group, a substituted or unsubstituted $C_1$-$C_{40}$ alkoxy group, a substituted or unsubstituted $C_2$-$C_{40}$ alkenyl group, a substituted or unsubstituted $C_2$-$C_{40}$ alkynyl group, a substituted or unsubstituted $C_4$-$C_{40}$ carbocyclic group, a substituted or unsubstituted $C_5$-$C_{40}$ carbocyclicalkyl group, a substituted or unsubstituted $C_4$-$C_{40}$ carbocyclic oxy group, and a substituted or unsubstituted $C_5$-$C_{40}$ carbocyclic alkyloxy group. At least one hydrogen atom of the hydrophobic moiety including 8 to 40 carbon atoms may be substituted with the same substituents described above in connection with the aryl group. In Formula (I), C may be a group having carbon numbers C8-C40, C8-C30, C8-C26, C8-C20, C8-C18, C8-C14, C10-C40, C10-C30, C10-C26, C10-C20, C10-C18, C10-C14, C12-C40, C12-C30, C12-C26, C12-C20, C12-C18, C12-C14, C14-C40, C14-C30, C14-C26, C14-C20, or C14-C18.

In Formula (I), C may be a $C_8$-$C_{40}$ alkyl group, for example, an alkyl group such as straight alkyl having carbon numbers C8, C10, C12, C14, C16, C18, C20, C22, C24, or C26. In addition, in Formula (I), C may be a sterol or a derivative thereof. The sterol or the derivative thereof may be cholesterol or a derivative thereof, or squalene or a derivative thereof.

The sonosensitizer may include, for example, a structural formula of

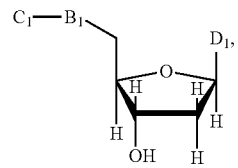

wherein $C_1$ may be a $C_8$-$C_{40}$ alkyl group, for example, an alkyl group such as straight alkyl having carbon numbers C8, C10, C12, C14, C16, C18, C20, C22, C24, or C26, $B_1$ may be —NH—C(O)—NH—, —O—C(O)—, —NH—C(O)—, —CH(COOH)—, or —NH—C(O)—O—, and $D_1$ is the same as described above. The sonosensitizer may have a structural formula of

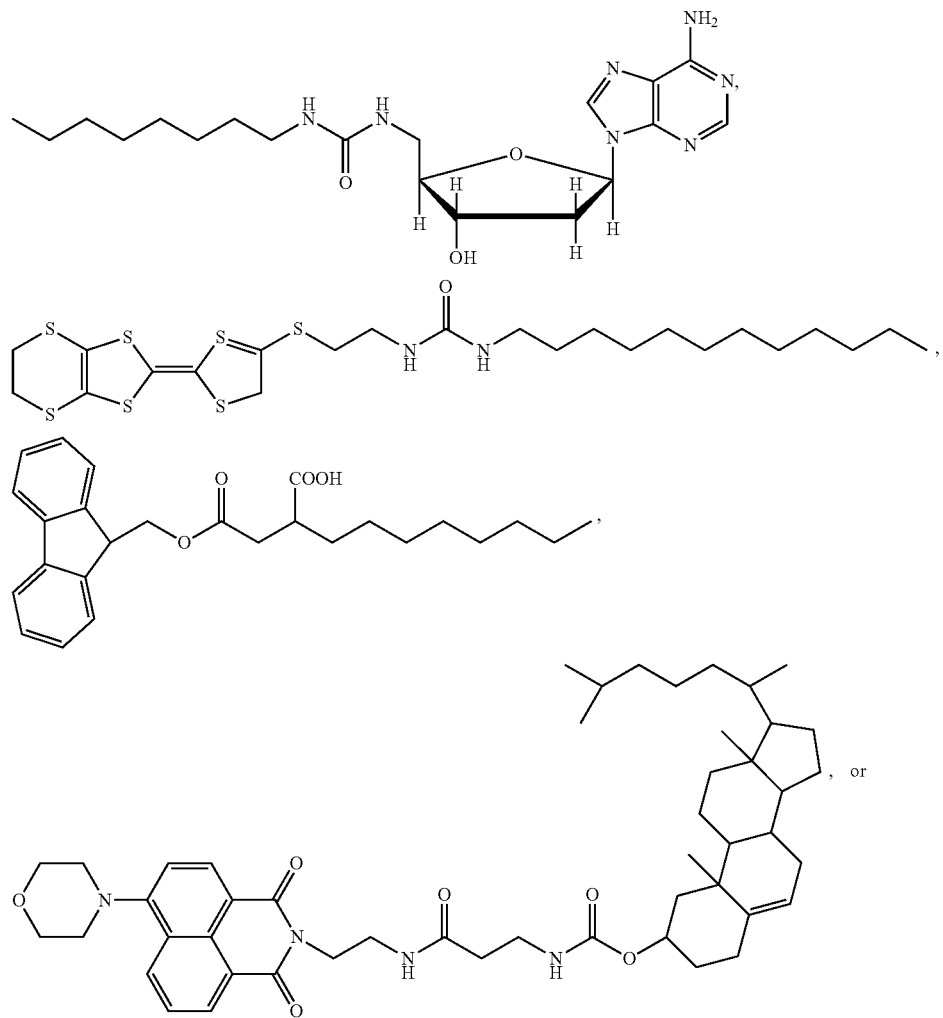

-continued

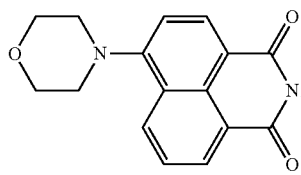 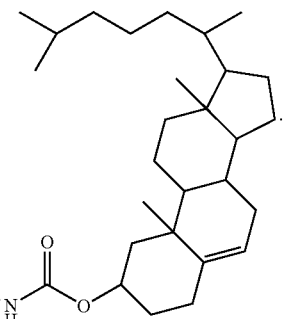

The sonosensitizer, in a state not exposed to ultrasound, may be contained in the liposome in a concentration less than a critical concentration at which the structure of the liposome may be destroyed. The sonosensitizer may be contained in the liposome in a range of from about 0.1% to about 20%, for example, about 0.1% to about 5%, about 1% to about 20%, about 2% to about 20%, about 4% to about 20%, about 6% to about 20%, about 8% to about 20%, about 10% to about 20%, about 1% to about 18%, about 1% to about 16%, about 1% to about 14%, about 1% to about 12%, about 1% to about 10%, about 1% to about 5%, about 2% to about 18%, about 2% to about 16%, about 2% to about 14%, about 2% to about 12%, about 2% to about 10%, or about 2% to about 5%, based on the total weight of the lipid molecules.

The sonosensitizer may not be a polymer including ethylene glycol. The polymer including ethylene glycol may be Triton™ X-100, Triton™ X-405, Tween™ 20, Tween™ 80, polyethylene glycol (PEG), polypropylene (PPO), a PEG triblock copolymer such as Pluronic P-105, or any combination thereof.

The liposome may further include an active agent. The active agent may be a pharmaceutical active agent, a magnetic active agent, an imaging agent, or any combination thereof. The active agent may be, for example, a compound, a protein, a peptide, nucleic acid, a nanoparticle, or any combination thereof. The active agent may include, for example, an anticancer agent, an anti-angiogenesis inhibitor, an anti-inflammatory agent, an analgesic, an antiarthritic, a dedative, an antidepressant, an antipsychotic agent, a tranquilizer, a tranquilizer, an antianxiety agent, a narcotic antagonist, an antiparkinson agent, a cholinergic agonist, an immunosuppressive agent, antiviral agent, an antibiotic, an appetite suppressant, an anticholinergic agent, an antihistamine, an anti-migraine agent, a hormone, a vasodilator, a contraceptive, an antithrombotic, a diuretic, an antihypertensive drug, a cardiovascular therapeutic, a wrinkle-diminishing agent, a skin aging inhibitor, a skin-whitening agent, or any combination thereof.

The active agent may be a hydrophobic drug, and examples thereof include sorafenib, paclitaxel, cyclosporine A, amphothericin B, indinavir, or any combination thereof. Sorafenib may be used as a therapeutic agent for renal cancer and liver cancer. Paclitaxel may be used as a therapeutic agent for ovarian cancer, breast cancer, or lung cancer. Cyclosporine A may be used as an immunosuppressive drug. Amphothericin B may be used as a polyene antibiotic. Indinavir may be used as a protease inhibitor. The hydrophobic active agent may be a steroid-based material, and examples thereof include glucocorticoid, a taxane-based drug, a cyclic peptide-based drug (e.g., cyclosporine A), indinavir, amphothericin B, or any combination thereof. Hydrophobic glucocorticoid may include, for example dexamethasone, trimacinolone, beclomethasone diproprionate, triamcinolone acetate, diacetate, bethamethasone diproprionate, testosterone, budesonide, 17α-ethinylestradiol, levonorgestrel, fluticasone proprionate, or any combination thereof. The active agent may be also a hydrophilic active agent. The term "hydrophilic" as used herein indicates properties of easy binding to water molecules, water solubility, or the nature of polarity. For example, the hydrophilic active agent may include methotrexate, doxorubicin, epirubicin, daunorubicin, vincristine, vinblastine, etoposide, ellipticine, camptothecin, docetaxel, cisplatin, prednisone, methyl-prednisone, biprobufen, idarubicine, valrubicin, mitoxantrone, ampicillin, streptomycin, penicillin, or any combination thereof.

The active agent may be a peptide drug, a protein drug such as an antibody, a biomolecule other than the peptide drug and the protein drug, or any combination thereof. Also, the active agent may be a combination of a chemical drug. The active agent may be, for example, Avastin® (Genentech/Roche), or a combination of Avastin® with chemotherapeutic agents, such as 5-fluorouracil, leucovorin, oxaliplatin, and irinotecan.

The term "imaging agent" as used herein is used interchangeably with the term "contrast media". The imaging agent refers to a material to enhance contrast of an image that shows tissues or blood vessels clearly at the time of examination such as magnetic resonance imaging (MRI) or computed tomography (CT) by artificially increasing absorption differences of each tissue or blood vessel. The imaging agent may be classified into a negative imaging agent and a positive imaging agent. The negative imaging agent allows more penetration than other surrounding tissues do, so as to show an image. For example, the positive imaging agent may be an iodine-containing imaging agent or barium sulfate, and the negative imaging agent may be air, gas, or carbon dioxide. The imaging agent may be a transitional element or a chelate complex of the transitional element. The transitional element may be, for example, La, Pr, Nd, Gd, Tb, Mn, Zn, Fe, Sc, Ti, V, Zn, Y, Zr, Nb, Mo, Pd, Ag, Cd, W, or Re. The transitional element may be in the form of ions. For example, gadolidium (atomic symbol Gd and atomic number 64) may be in the form of $Gd^{3+}$. A chelate complex of Gd may include, for example, gadoteric acid, gadodiamide, gadobenic acid, gadopentetetic acid, gadoteridol, gadoversetamide, gadoxetatic acid, gadobutrol, or any combination thereof.

The active agent may be contained in an interior space of the liposome, in an interior of the lipid bilayer, or in both.

The liposome may have a diameter of 20 nm or greater, for example, in a range from about 50 nm to about 500 nm, about 50 nm to about 400 nm, about 50 nm to about 300 nm, about 50 nm to about 200 nm, or about 50 nm to about 150 nm. The liposome may be in a form of unilamellar vesicles (SUVs) or multivesicular vesicles.

The liposome may be manufactured according to methods widely known in the art. The liposome may be manufactured by a method using a thin film hydration technique. The liposome may use an aqueous solution thereof as a hydrating fluid of water-soluble (hydrophilic) materials, or may add a drug or a drug solution at any step in the manufacturing of the liposome, thereby manufacturing a liposome in which the water-soluble materials are entrapped. In addition, fat-soluble (hydrophobic) materials may be prepared by which the materials are dissolved in an organic solution of a configuration lipid, and the mixed solution is evaporated to obtain a dried lipid film containing drugs and to be hydrated. Such methods are related to a step of loading an active agent (i.e., a passive loading) before or during the manufacturing of the liposome. However, a specific type of compound, such as a compound having an ionizable group or a material having both lipid and water solubility, may be introduced into the liposome (i.e., a remote loading) after these specific type of compounds are formed as intact vesicles. An example of the remote loading includes an ammonium sulfate gradient method (*J. Control. Release* 2009, 139, 73-80).

According to another aspect of the present disclosure, a pharmaceutical composition for delivering an active agent to a subject includes a liposome including a lipid bilayer, a sonosensitizer disposed on the lipid bilayer, and an active agent, wherein the sonosensitizer self-assembles to form aggregates, when exposed to ultrasound.

A detailed description of the sonosensitive liposome including the lipid bilayer and the sonosensitizer disposed on the lipid bilayer, wherein the sonosensitizer self-assembles to form aggregates, when exposed to ultrasound, has been already described above.

The pharmaceutical composition may further include a pharmaceutically acceptable carrier or diluent. The pharmaceutically acceptable carrier or diluent may be well known in the art, and examples thereof include lactose, dextrose, sucrose, sorbitol mannitol, starch, acacia gum, calcium phosphate, alginate, gelatin, calcium silicate, microcrystalline cellulose, polyvinylpyrrolidone, cellulose, water (e.g., saline or sterile water), syrup, methyl cellulose, methylhydroxybenzoate, propylhydroxybenzoate, talc, magnesium stearate, mineral oil, Ringer's solution, buffer, maltodextrin solution, glycerol, ethanol, or any combination thereof. The pharmaceutical composition may further include a lubricant, a wetting agent, a sweetening agent, a flavoring agent, an emulsifier, a suspending agent, a preserving agent, or any combination thereof.

According to methods that are known in the art, the pharmaceutical composition may be formulated and prepared in the form of a unit dose using the pharmaceutically acceptable carrier and/or diluents, or may be introduced and prepared in a multi-dose container. Here, the pharmaceutical composition may be formulated in types of a solution of oil or aqueous medium, suspension, syrup, or emulsion. In some embodiments, the pharmaceutical composition may be formulated in types of extracts, powders, powdered drugs, granules, tablets, or capsules. The pharmaceutical composition may further include a dispersant or a stabilizer. The aqueous medium may contain physiological saline or PBS.

According to another aspect of the present disclosure, a method of delivering an active agent into the body of a subject includes administering a pharmaceutical composition including a liposome including a lipid bilayer, a sonosensitizer disposed on the lipid bilayer, and an active agent, wherein the sonosensitizer self-assembles to form aggregates, when exposed to ultrasound; and applying ultrasound to the subject to release the active agent.

The method includes administering the pharmaceutical composition including the liposome including the lipid bilayer, the sonosensitizer disposed on the lipid bilayer, and the active agent, wherein the sonosensitizer self-assembles to form aggregates, when exposed to ultrasound.

A detailed description of the liposome including the lipid bilayer, the sonosensitizer disposed on the lipid bilayer, and the active agent has been already described above.

The subject may be a mammal, and the mammal may be a primate mammal. The subject may be a human, a cow, a pig, a horse, a rabbit, a mouse, or a combination thereof.

The administration may be, for example, oral administration or parenteral administration. The parenteral administration may be, for example, intravenous, intramuscular, intracavity (abdominal cavity, joints, or eyes), or direct injection. The direct injection may involve injecting directly into a diseased site such as a tumor site. The liposome may be administered intravenously, and accordingly, brought to the target site such as a tumor site by blood flow. The target site may have a leaky property. Dosage of the liposome may be prescribed according to various factors such as formulation methods, administration methods, patient's age, weight, gender and morbidity, foods, administration times, administration routes, excretion rates, and reaction sensitivity. Dosage of the liposome may be in a range from about 0.001 mg/kg to about 100 mg/kg, for example, about 0.01 mg/kg to about 100 mg/kg, about 0.1 mg/kg to about 100 mg/kg, about 1 mg/kg to about 100 mg/kg, about 10 mg/kg to about 100 mg/kg, about 50 mg/kg to about 100 mg/kg, about 0.001 mg/kg to about 50 mg/kg, about 0.01 mg/kg to about 10 mg/kg, about 0.1 mg/kg to about 1 mg/kg, about 1 mg/kg to about 10 mg/kg, or about 1 mg/kg to about 50 mg/kg.

The administration may be carried out in various ways including use of a catheter. The catheter is a device that may be inserted into a subject, and more particularly, a tubular structure like blood vessels, digestive tracts, ureters, and reproductive organs. A typical structure of the catheter is known in the art. The catheter is typically flexible and has a tubular main body including one or more lumens extending through the tubular main body. In order to inject liposome-like vesicles into a subject, there may be a port placed at a terminus of the catheter. Attachment of an ultrasound imaging probe to the catheter may be helpful in visualizing an inner wall of the tubular structure of the subject, to deliver the liposomes containing active agents such as a therapeutic agent or a diagnostic agent to a guided and targeted specific area of the subject. A material that specifically binds to a target cell may be, for example, an antibody that specifically binds to an antigen present on the surface of the target cell, or a liposome to which an antigen-binding fragment thereof is bound, and such a material may specifically bind to a target cell. In addition, a material that specifically binds to a substance in the body fluid may be, for example, an antibody that specifically binds to an antigen of the body fluid, or a liposome to which an antigen-binding fragment thereof is bound, and such a material may be specifically moved to a specific body fluid.

The administration may be site-specific administration in the subject. The specific site may include tumor or brain.

The method includes applying ultrasound to the target site of the subject to release the active agent.

Ultrasound may be irradiated at amplitudes of 5% to 100% or 20% to 100% of the maximum amplitude. Ultrasound may be irradiated so as to have an output range from about 10 W/cm² to about 15 kW/cm².

Ultrasound may be applied to the subject for about 1 to about 20 minutes, for example, about 5 to about 15 minutes. The ultrasound may be randomly applied to the entire subject, or applied to a specific site of the subject.

One or more embodiments of the present disclosure will now be described more fully with reference to the following examples. However, these examples are provided only for illustrative purposes and are not intended to limit the scope of the present disclosure.

Example 1

Sonosensitive Liposome Size and Drug Release, According to Types of Phospholipids Liposomes including sonosensitizers were prepared. Then, it was confirmed that sizes of the liposomes were changed according to the amount of the sonosensitizers, and sizes of the liposomes and drug release of the liposomes were changed when exposed to ultrasound. A 2'-deoxyadenosine derivative having a urea linker and an octyl hydrocarbon tail of Formula 2 below, was used as the sonosensitizer. The 2'-deoxyadenosine derivative was synthesized according to methods described in the literature (Soft matter, 2008, 4, 1995-1997).

(2)

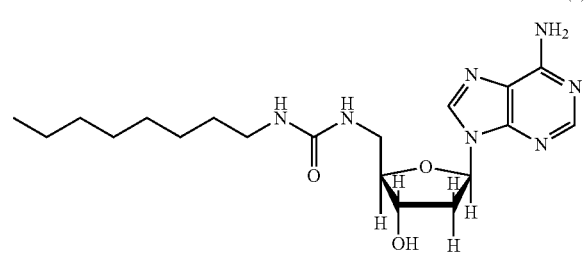

Doxorubicin (DX) was loaded on the liposomes according to the ammonium sulfate gradient method (*J. Control. Release* 2009, 139, 73-80).

In greater detail, liposomes in a form of unilamellar vesicles were prepared using a lipid thin film hydration method as follows. First, 1,2-dipalmitoyl-sn-glycero-3-phosphocholine (DPPC) or 1,2-distearoyl-sn-glycero-3-phosphocholine (DSPC), 1,2-distearoyl-sn-glycero-3-phosphoethanolamine-N-[methoxy(polyethylene glycol)-2000] (ammonium salt) (DSPE-PEG), and cholesterol were obtained from Avanti Polar Lipid company (USA)). A 2'-deoxyadenosine derivative having an octyl hydrocarbon tail including a urea moiety of Formula above was used as the sonosensitizer. The 2'-deoxyadenosine derivative was synthesized according to methods described in the literature (Soft matter, 2008, 4, 1995-1997). DPPC/DSPC, DSPE-PEG 2000, cholesterols, and sonosensitizer were prepared in a molar ratio of 55:2:15:0.55, and dissolved in chloroform in a round-bottom flask. The total lipid concentration was about 9.6 mg/ml. A lipid thin layer was formed on the interior wall of the flask by evaporating chloroform at room temperature under reduced pressure using a rotary evaporator.

Next, the lipid thin layer was hydrated by adding a 250 mM ammonium sulfate solution (pH 4.0) to the flask, and the hydrated solution was subjected to vortexing. Unilamellar vesicle type liposomes were prepared by filtering the hydrated solution at room temperature through a polycarbonate film with pores having a size of 100 nm.

A liposome solution formed of liposomes with 250 nM of ammonium sulfate inside and 25 mM of Tris.HCl outside by passing the prepared unilamellar vesicle type liposomes solution through a PD-10 desalting column (GE Healthcare) including Sephadex™ G-25 medium filled with 25 nM of Tris.HCl (pH 9.0) (Sample 1). 100 ul (10 mg/ml) of doxorubicin (DX) was added to the obtained liposome solution, and then, incubated for an hour at a temperature of 37° C. (in a mass ratio of 1:0.2 to the main lipid components). The prepared liposome solution was passed through a PD-10 Desalting Column (GE Healthcare) including Sephadex™ G-25 medium filled with PBS buffer to remove unsealed DX. As a result, liposomes in which DX was entrapped in the aqueous interior were prepared (Sample 2). The sizes of the liposome particles in the prepared Samples 1 and 2 were measured by a Zeta-sizer device (Malvern inst.) using dynamic light scattering (DLS). The results of the sizes of the liposome particles were shown in Table 1 below.

TABLE 1

| Primary lipid | Sample 1 | | Sample 2 | |
|---|---|---|---|---|
| | d (nm) | Pdi | d (nm) | Pdi |
| DPPC | 166.6 | 0.0475 | 169.3 | 0.087 |
| DSPC | 183.3 | 0.1305 | 186.55 | 0.111 |

Referring to Table 1, Samples 1 and 2 each showed the liposomes with unsealed DX and liposomes with sealed DX, and d and Pdi each indicated a diameter and a number polydispersity index of the liposome particles. As shown in Table 1, the sizes of the liposomes were different according to the types of the primary lipids, and the injection of DX did not induce significant changes in the particle sizes.

Example 2

Changes in Liposome Sizes According to Exposure Time to Ultrasound

Liposomes were prepared according to the same method used in Example 1, except that DPPC, DSPE-PEG, cholesterols and sonosensitizers were prepared in a molar ratio of 55:2:15:0.55, 55:2:15:1.1, or 55:2:15:2.75. In this case, senosensitizers contents in mol % with respect to DPPC is 1%, 2% and 5%, respectively.

Then, the sizes of the prepared liposomes were measured according to the same method used in Example 1. In addition, dispersions of the prepared liposomes were diluted using a PBS buffer in a ratio of 1:10 by volume, and 5 ml of the diluted solution was put in a sample chamber of a Vibra Cell ultrasonic processor (VCX 130, Sonics & Materials Inc.). Here, ultrasound having a frequency of 20 kHz and an output of 130 W was applied thereto for a specified period of time. Ultrasound was applied thereto at amplitudes of 100% to 50% of the maximum amplitude. Tables 2 and 3 each showed changes in the sizes of the liposomes according to the amounts of sonosensitizers (Table 2) and the exposure time to ultrasound (Table 3).

TABLE 2

| Amounts of sonosensitizer | Sample 1 | | Sample 2 | |
|---|---|---|---|---|
| (mol %) | d (nm) | Pdi | d (nm) | Pdi |
| 1 | 174.8 | 0.0475 | 169.3 | 0.087 |
| 2 | 170.15 | 0.0355 | 171.15 | 0.085 |
| 5 | 166.45 | 0.0575 | 165.15 | 0.0945 |

Referring to Table 2, Samples 1 and 2 each showed liposomes with unsealed DX and liposomes with sealed DX, and d and pdi each indicated a diameter and a number polydispersity index of the particles. In Table 2, the amounts of the sonosensitizers were indicated in mol % with respect to the main lipid DPPC. As shown in Table 2, as the amounts of the sonosensitizers increased, the liposome particle sizes were found to be smaller. Data in Table 2 were obtained by measuring the sizes of the liposomes prepared according to the amounts of the sonosensitizers, and the sizes of the liposomes with unsealed DX without application of ultrasound.

TABLE 3

| Ultrasound exposure | Sample 1 | |
|---|---|---|
| time (minutes) | d (nm) | Pdi |
| 1 | 164.6 | 0.1105 |
| 2 | 164.2 | 0.117 |
| 5 | 164.9 | 0.074 |
| 10 | 165.05 | 0.062 |

Referring to Table 3, Sample 1 showed the liposomes with unsealed DX, and d and Pdi each indicated a diameter and a number polydispersity index of the particles. As shown in Table 3, it was confirmed that the sizes of the liposomes were not changed according to the exposure time to ultrasound. As a result, it was confirmed that the liposomes did not destroy themselves in spite of the exposure to ultrasound.

It was also confirmed that the drug release from the liposomes with sealed DX was changed (increased) according to the exposure time to ultrasound (see FIG. 1). As a result, it was confirmed that the drug release may be induced by the exposure to ultrasound.

Example 3

Changes in Drug Release of Liposomes According to Molar Ratios of Sonosensitive Molecules and Stimulus Applied Thereto Liposomes were prepared according to the same method used in Example 1, except that DPPC, DSPE-PEG, cholesterols and sonosensitizers were prepared in a molar ratio of 55:2:15:0.275, 55:2:15:0.55, 55:2:15:1.1, 55:2:15:1.65, 55:2:15:2.2, or 55:2:15:2.75.

The drug release of the prepared liposomes were measured by applying ultrasound (having a frequency of 20 kHz and an output of 130 W) thereto, according to the same method used in Example 2, and measuring the extent of the drug release according to DX fluorescence using a fluorescence spectrometer (PerkinElmer, Envision 2104-multilabel reader). The measured fluorescence was indicated as a percentage with respect to the total amount of DX. In greater detail, after ultrasound was applied to the liposomes, the fluorescent intensity of the sample was appropriately diluted to determine the amounts of DX released from the liposomes, and then measured at an excitation wavelength ($\lambda$ex) of 485 nm and an emission wavelength ($\lambda$em) of 635 nm. The relative percentage in fluorescence intensity (% release) according to the application of ultrasound during a specific period of time was calculated based on the total release of the entrapped substances that were obtained after the destruction of the liposomes by adding 1% Triton X-100 (ethanol). Percent (%) release was calculated according to Equation below.

% release=$(Ft-Fi)/(Ff-Fi) \times 100$ (*Ft is a fluorescence value measured according to the ultrasound exposure time; Fi is a fluorescence value measured before the ultrasound exposure; and Ff is 1% Triton X in EtOH)

In addition, in order to confirm the thermal stability of the same liposomes, the prepared liposomes were incubated for one hour at a temperature of 37° C., and the amount of the DX released therefrom were measured as described above.

FIG. 1 is a graph showing the extent of drug release according to amounts of the sonosensitizers and ultraspound exposure time. In FIG. 1, the amounts of the sonosensitizers were indicated in mol % with respect to the main lipid DPPC. As shown in FIG. 1, the extent of the drug release varies according to the amounts of the sonosensitizers, and thus, the extent of the drug release may be controlled by adjusting the amounts of the sonosensitizers.

When the liposomes containing DX including a 2 mol % sonosensitizer were exposed to ultrasound for about 3 minutes, the drugs of about 90% or more has been released. In FIG. 1, the US exposure time on the horizontal axis indicates the exposure times to ultrasound and the Dox release on the vertical axis indicates the extents of the Dox release, and 0.5 mol %, 1 mol %, 2 mol %, 3 mol %, 4 mol %, and 5 mol % indicate the amounts of the sonosensitizers.

Table 4 is the result of FIG. 1.

TABLE 4

| Exposure time to ultrasound (minute) | Amounts of sonosensitizer | | | | | |
|---|---|---|---|---|---|---|
| | 0.5% | 1% | 2% | 3 | 4 | 5 |
| | | | DX release (%) | | | |
| 1 | 19.8 | 31.6 | 35.9 | 27.9 | 24.3 | 22.6 |
| 3 | 46.3 | 54.0 | 87.5 | 54.0 | 50.9 | 56.5 |
| 5 | 65.7 | 66.4 | 89.6 | 66.3 | 62.4 | 76.1 |
| 10 | 84.2 | 76.8 | 85.2 | 72.2 | 75.09 | 90.5 |

Table 5 shows the extent of the drug release measured when the liposomes containing the sonosensitizers and DX were incubated for one hour at a temperature of 37° C.

TABLE 5

| Amounts of sonosensitizer (mol %) | Drug release (%) |
|---|---|
| 0.5 | 0 |
| 1 | 0.7386 |
| 2 | 2.8601 |
| 3 | 1.3585 |
| 4 | 0.8075 |
| 5 | 0.5267 |

Referring to Table 5, the extent of the drug release was found to be less than about 2.9%, which means that the drug only barely released. Therefore, it was confirmed that the liposomes were not sensitive to temperature changes, and the permeability thereof was changed according to the exposure to ultrasound.

Example 4

Observation of Cellular Uptake of Sonosensitive Liposome-Treated Cells

Liposomes were prepared according to the same method used in Example 1, except that DPPC, DSPE-PEG, cholesterols and sonosensitizers were prepared in a molar ratio of 55:2:20:1.65. The drug release of the prepared liposomes was induced by applying ultrasound (having a frequency of 20 kHz and an output of 130 W, at 50% amplitude) thereto for a given time 5 minutes, according to the same method used in Example 2. Hela cells were grown in a 5% $CO_2$ incubator filled with DMEM (Gibco) supplemented with 10% bovine serum albumin (BSA) at a temperature of 37° C. 10%. All cells were subcultured twice a week. The cells were seeded per well in concentration of $1 \times 10^6$ cells in a 12-well plate. The cells grew for 24 hours, so as to have a confluence of about 80% before the experiment. The cells were washed twice with a DMEM culture medium, and then, 10 ul of the sonicated liposomes (DX concentration of 20 ug/ml) was immediately added to each well of the plate, and incubated for 30 minutes under the same conditions. Next, the fluorescence intensity coming from the cells were measured by a confocal microscope (LSm 710, Carl Zeiss, USA). As a result, the drugs released by the exposure to ultrasound, and the cellular uptake of the released drugs were confirmed. When the ultrasound was applied at an amplitude of 50% of the maximum amplitude and at a frequency of 20 kHz to the liposomes, the drug release and the cellular uptake were increased proportional to the exposure time to ultrasound. When the liposomes were exposed to ultrasound for more than 1 minute, the extent of the drug release and the cellular uptake were similarly shown.

The same liposomes were exposed to ultrasound for 5 minutes at different amplitudes (i.e., 50%, 75%, and 100% of the maximum amplitude) at a frequency of 20 kHz. 10 ul of the sonicated liposomes (DX concentration of 20 ug/ml) was immediately added to Hela cells as described above, and then, incubated for 30 minutes. As a control group, a group treated with 10 ul of PBS, a group treated with 10 ul of radical DX (20 ug/ml of distilled water), and a group wherein HeLa cells are incubated at a temperature of 42° C. were all included. The cell viability thereof was obtained by counting viable cells using a WST assay [2-(2-methoxy-4-nitrophenyl)-3-(4-nitrophenyl)-5-(2,4-disulfophenyl)-2H-tetrazolium, monosodium salts] (WST-8, Cell Counting Kit-8, Dojindo, Japan).

Figure 2:
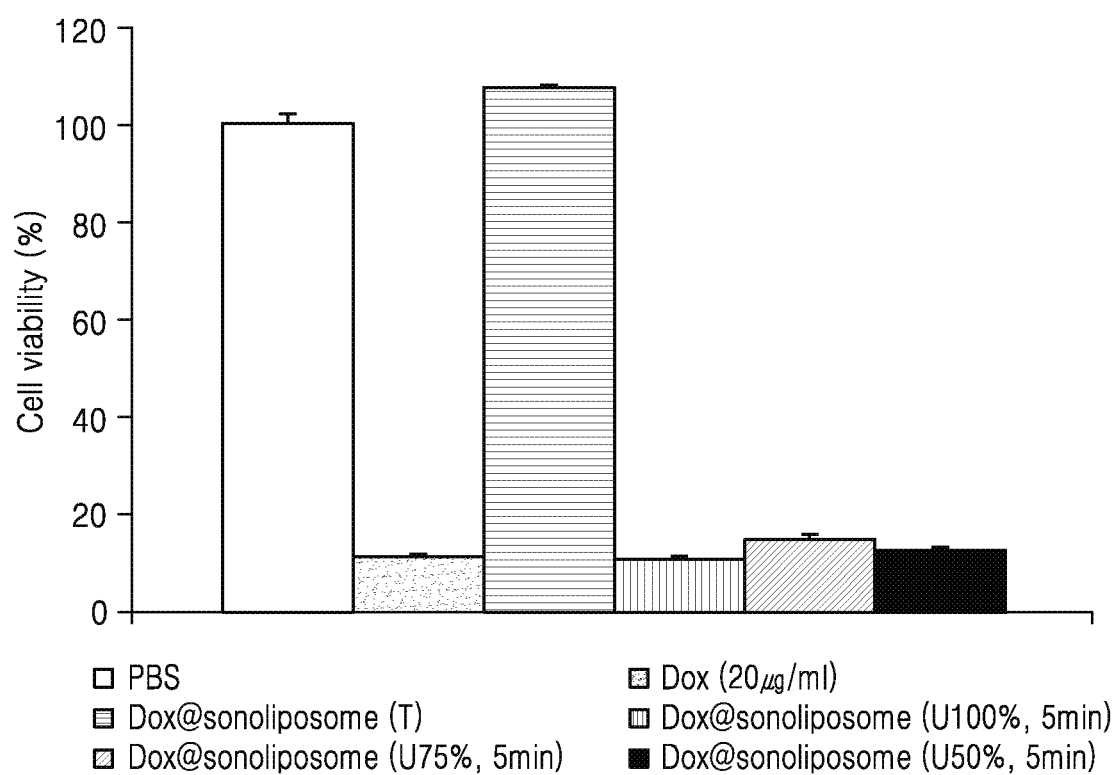
FIG. 2 is a graph showing the effects of liposomes on cell viability, the liposomes containing drugs and being sonicated at various amplitudes.

FIG. 2 is a graph showing effects of liposome on cell viability, the liposomes containing drugs that are irradiated at various amplitudes. As shown in FIG. 2, in the case of exposure to ultrasound for 5 minutes at an amplitude of 50% (Dox@sonoliposome (U50%, 5 min)), 75% (Dox@sonoliposome (U75%, 5 min)), and 100% (Dox@sonoliposome (U100%, 5 min)) of the maximum amplitude, and at a frequency of 20 kHz, the cell viability of the liposomes was about 15% compared to that of the control group (in which DX was not treated), and that is, the cell viability of the liposomes was similar with that of the liposomes in which radical Dx was treated. Meanwhile, in a case that Hela cells were incubated at a temperature of 42° C. without ultrasound treatment or any other treatment, the cell viability thereof was more than about 100. Thus, it was confirmed that the liposomes did not destroy themselves at a temperature of 42° C., or the permeability thereof did not increase at a temperature of 42° C. In FIG. 2, the PBS indicates a group treated with 10 ul of PBS only, the Dox (20 ug/ml) indicates a group treated with 10 ul of radical DX (20 ug/ml of distilled water), the Dox@sonoliposome (T) indicates a group treated with HeLa cells at a temperature of 42° C., the Dox@sonoliposome (U50%, 5 min), the Dox@sonoliposome (U75%, 5 min), and the Dox@sonoliposome (U100%, 5 min) each indicates ultrasound exposure for 5 minutes at an amplitude of 50%, 75%, and 100% of the maximum amplitude and at a frequency of 20 kHz.

As described above, the liposomes including the sonosensitizers do not destroy themselves at temperature changes nor increase the permeability thereof. However, the liposomes increase the permeability thereof in response to ultrasound. In this regard, the liposomes may deliver drugs to a subject according to ultrasound-specific ways.

As described above, according to the one or more of the above embodiments of the present disclosure, a sonosensitive liposome and a pharmaceutical composition including the same may be used to efficiently deliver the liposome or an active agent contained therein. According to another or more of the above embodiments of the present disclosure, a method of delivering the active agent to a target site in the body of a subject may be used to efficiently deliver the active agent to the target site in the body of the subject.

It should be understood that the exemplary embodiments described therein should be considered in a descriptive sense only and not for purposes of limitation. Descriptions of features or aspects within each embodiment should typically be considered as available for other similar features or aspects in other embodiments. While one or more embodiments of the present disclosure have been described with reference to the figures, it will be understood by those of ordinary skill in the art that various changes in form and details may be made therein without departing from the spirit and scope of the present disclosure as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A liposome comprising:
   a lipid bilayer;
   a sonosensitizer that is disposed in the lipid bilayer; and
   an active agent contained in an interior space of the liposome, an interior of the lipid bilayer, or both,
   wherein the sonosensitizer self-assembles to form aggregates and the active agent is released when the liposome is exposed to ultrasound, and wherein the sonosensitizer has a structural formula of

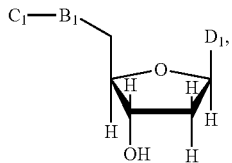

wherein $C_1$ is a $C_8$-$C_{40}$ alkyl group, $B_1$ is —NH—C(O)—NH—, —NH—C(O)—, —CH(COOH)—, or —NH—C(O)—O—, and $D_1$ is

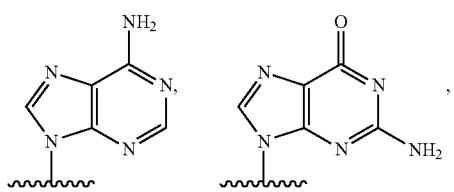

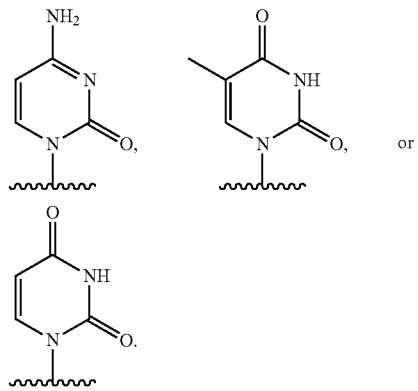

2. A liposome comprising:
   a lipid bilayer; and
   a sonosensitizer that is disposed in the lipid bilayer,
   wherein the sonosensitizer self-assembles to form aggregates when exposed to ultrasound, and wherein the sonosensitizer has a structural formula of

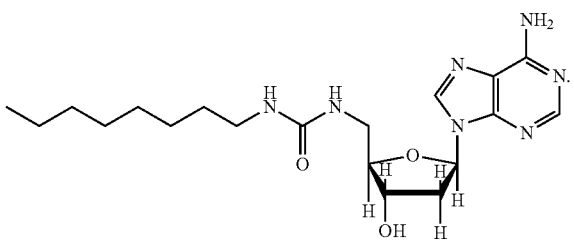

3. The liposome of claim 2, further comprising an active agent.

4. The liposome of claim 2, wherein the active agent is a pharmaceutical active agent, a magnetic active agent, an imaging agent, or any combination thereof.

5. The liposome of claim 2, wherein the active agent is contained in an interior space of the liposome, in an interior of the lipid bilayer, or in both.

6. The liposome of claim 3, wherein the active agent is a pharmaceutical active agent.

7. The liposome of claim 3, wherein the active agent is an imaging agent.

8. The liposome of claim 3, wherein the active agent is a magnetic agent.

* * * * *